US009259536B2

(12) United States Patent
Gillespie, III et al.

(10) Patent No.: US 9,259,536 B2
(45) Date of Patent: Feb. 16, 2016

(54) AUTOMATIC INJECTION SYRINGE ASSEMBLY WITH INTEGRATED, FILLABLE MEDICINE CONTAINER AND METHOD OF FILLING AN INJECTION SYRINGE ASSEMBLY

(75) Inventors: Richard David Gillespie, III, Athens, TX (US); Doug Owen Crow, Brownsboro, TX (US)

(73) Assignee: West Pharmaceutical Services, Inc., Exton, PA (US)

(*) Notice: Subject to any disclaimer, the term of this patent is extended or adjusted under 35 U.S.C. 154(b) by 555 days.

(21) Appl. No.: 13/639,335

(22) PCT Filed: Apr. 20, 2011

(86) PCT No.: PCT/US2011/033253
§ 371 (c)(1),
(2), (4) Date: Oct. 4, 2012

(87) PCT Pub. No.: WO2011/133672
PCT Pub. Date: Oct. 27, 2011

(65) Prior Publication Data
US 2013/0030384 A1    Jan. 31, 2013

Related U.S. Application Data

(60) Provisional application No. 61/326,034, filed on Apr. 20, 2010.

(51) Int. Cl.
*A61M 5/31* (2006.01)
*A61M 5/315* (2006.01)
(Continued)

(52) U.S. Cl.
CPC ......... *A61M 5/31596* (2013.01); *A61M 5/1782* (2013.01); *A61M 5/2033* (2013.01);
(Continued)

(58) Field of Classification Search
CPC .......... A61M 5/31526; A61M 5/3129; A61M 5/1782; A61M 5/31511; A61M 5/2448; A61M 5/284; A61M 5/285; A61M 5/288; A61M 5/20; A61M 2005/3121; A61M 2005/3114; A61M 2005/2437; A61M 5/2033; A61M 5/31596; A61J 1/065; A61J 1/1481; A61J 1/2096
See application file for complete search history.

(56) References Cited

U.S. PATENT DOCUMENTS 5,067,948 A * 11/1991 Haber et al. .................. 604/213
5,298,024 A    3/1994 Richmond
(Continued)

FOREIGN PATENT DOCUMENTS

EP    112574 A1    7/1984
EP    363338 A3    9/1990
(Continued)

OTHER PUBLICATIONS

International Search Report issued Oct. 28, 2011 in International Application No. PCT/US2011/033253.
(Continued)

*Primary Examiner* — Nathan R Price
*Assistant Examiner* — Justin L Zamory
(74) *Attorney, Agent, or Firm* — Panitch Schwarze Belisario & Nadel LLP

(57) ABSTRACT

An automatic injection syringe assembly having an integrated and fillable medicine container that includes a medicine container within a housing and a conduit assembly. The medicine container includes a piston having an aperture at a distal end thereof for the passage of fluid therethrough. The conduit assembly includes a conduit member that is releasably connected to the housing and has an open proximal end and an open distal end. The open distal end of the conduit member is releasably engaged with the piston and in fluid communication with the piston aperture. The open proximal end and the open distal end of the conduit member are m fluid communication via a conduit within the conduit member.

10 Claims, 12 Drawing Sheets

(51) Int. Cl.
  *A61M 5/178* (2006.01)
  *A61M 5/20* (2006.01)
  *A61M 5/24* (2006.01)
  *A61M 5/32* (2006.01)

(52) U.S. Cl.
  CPC ......... *A61M5/31511* (2013.01); *A61M 5/2466* (2013.01); *A61M 5/3129* (2013.01); *A61M 5/326* (2013.01); *A61M 2005/206* (2013.01); *A61M 2005/3128* (2013.01)

(56) References Cited

U.S. PATENT DOCUMENTS

| | | | | |
|---|---|---|---|---|
| 5,569,191 A | * | 10/1996 | Meyer | A61F 9/0008 604/201 |
| 5,665,071 A | | 9/1997 | Wyrick | |
| 5,785,683 A | | 7/1998 | Szapiro et al. | |
| 5,807,323 A | * | 9/1998 | Kriesel | A61M 5/14526 604/232 |
| 6,280,430 B1 | * | 8/2001 | Neftel et al. | 604/411 |
| 2006/0079834 A1 | * | 4/2006 | Tennican et al. | 604/88 |
| 2010/0036320 A1 | | 2/2010 | Cox et al. | |

FOREIGN PATENT DOCUMENTS

| | | |
|---|---|---|
| FR | 2082128 A5 | 12/1971 |
| GB | 2461086 A | 12/2009 |
| GB | 2461087 B | 9/2012 |
| JP | 2003341749 A | 12/2003 |
| WO | 2009136209 A1 | 11/2009 |

OTHER PUBLICATIONS

Int'l Preliminary Report on Patentability issued Nov. 1, 2012 in Int'l Application No. PCT/US2011/033253.

* cited by examiner

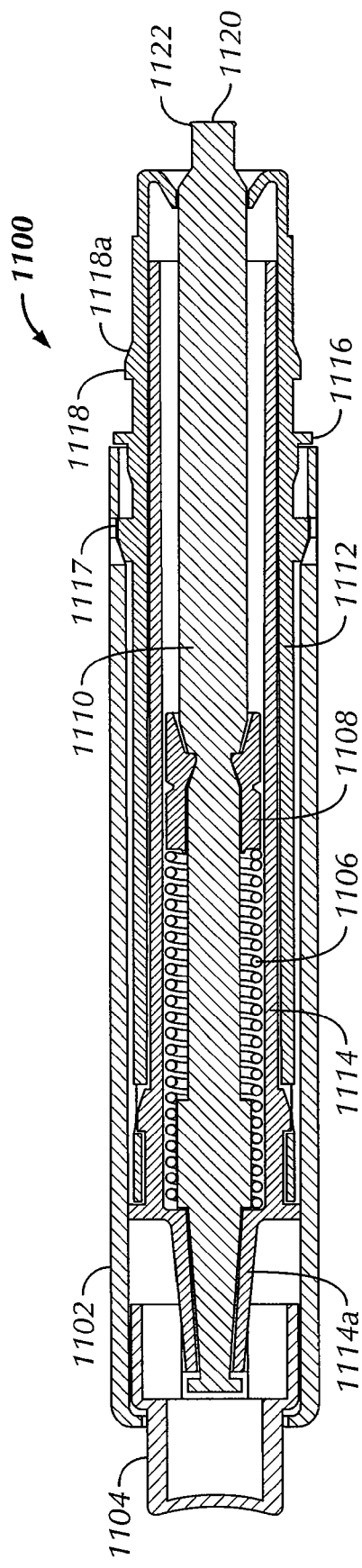
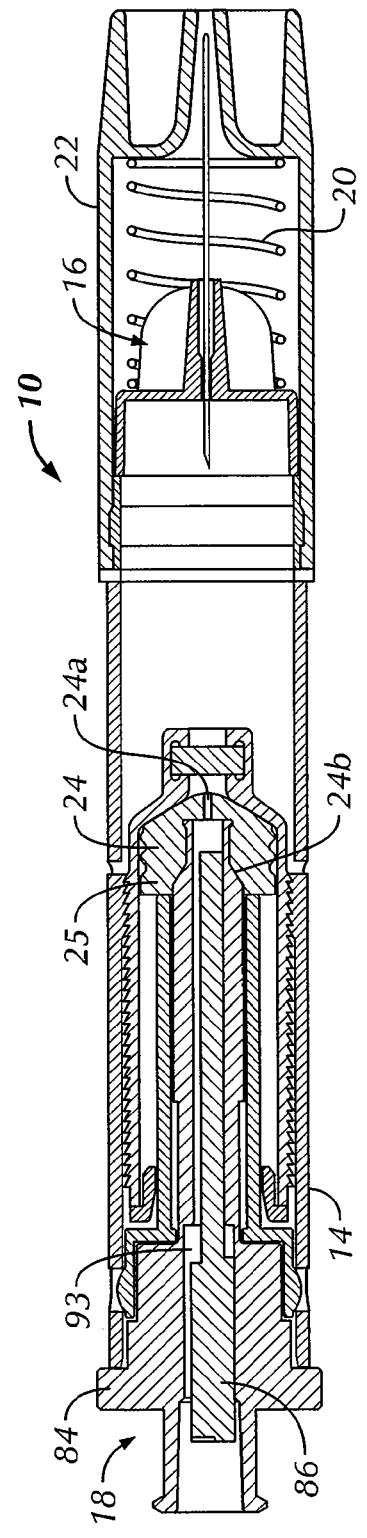
FIG. 2A
FIG. 2B

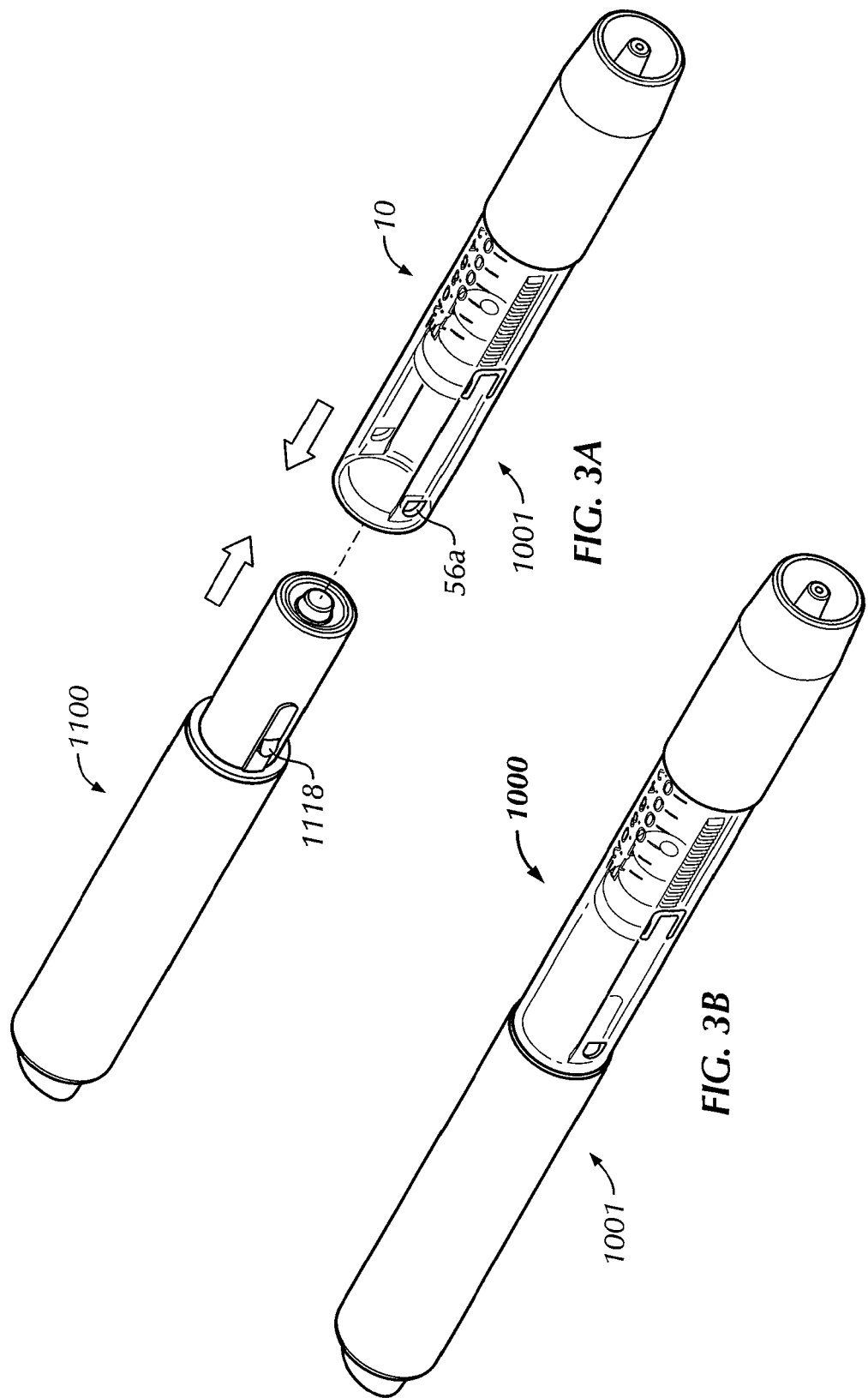

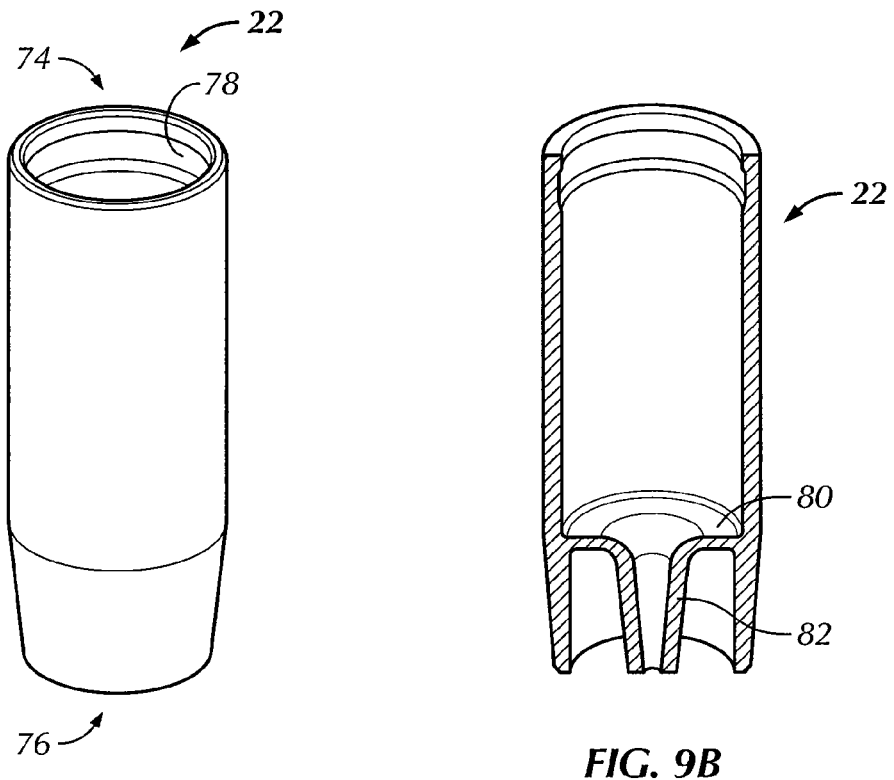
FIG. 9A
FIG. 9B
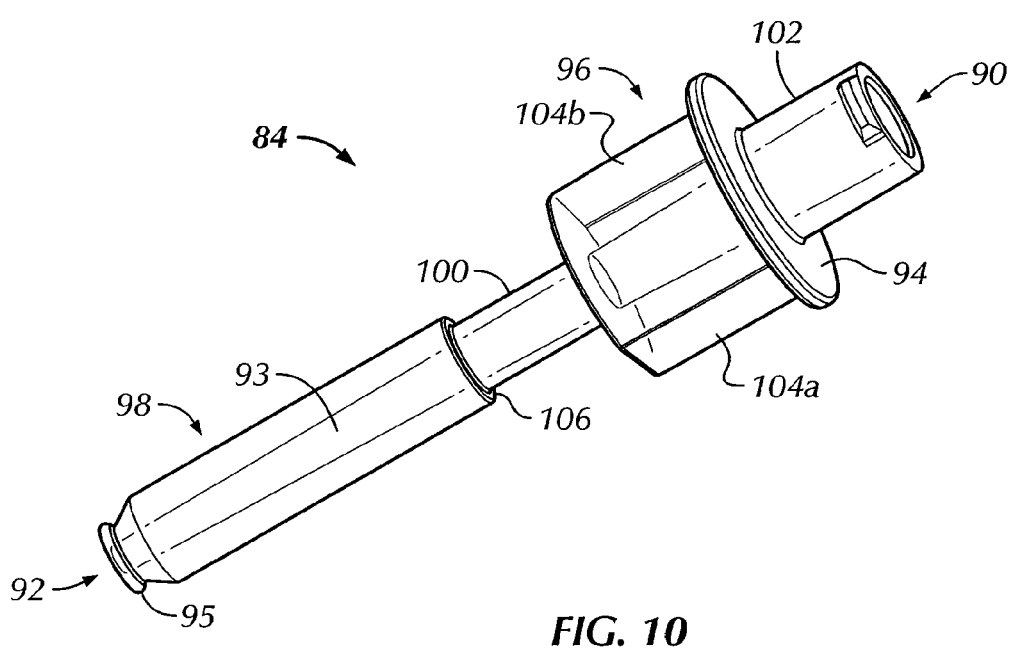
FIG. 10

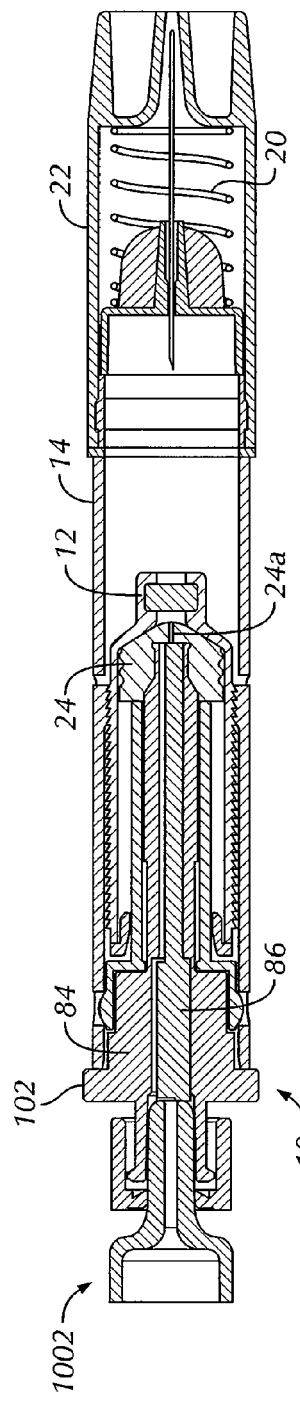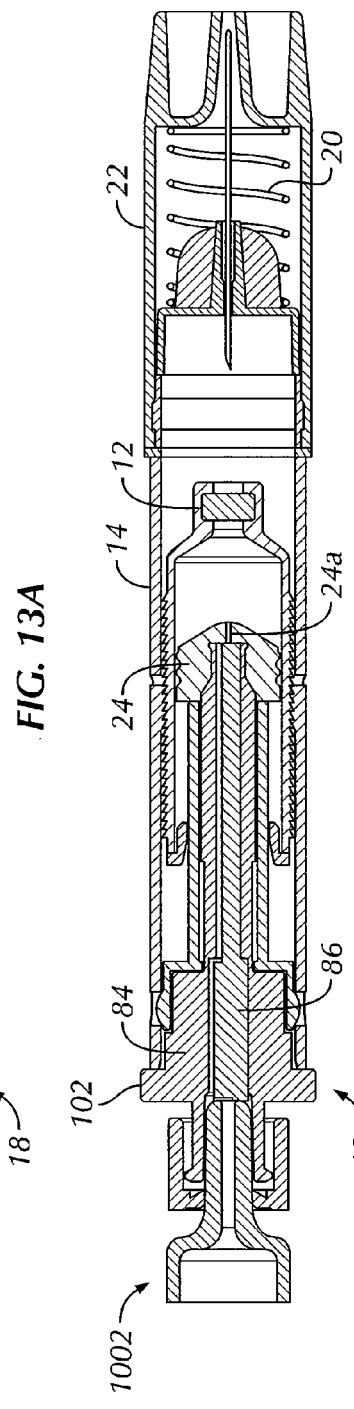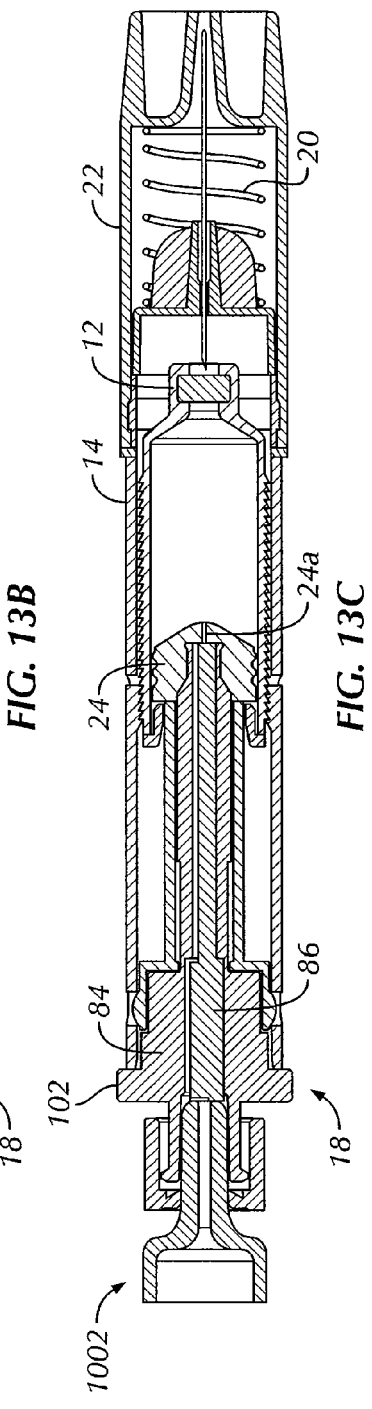
FIG. 13A
FIG. 13B
FIG. 13C

AUTOMATIC INJECTION SYRINGE ASSEMBLY WITH INTEGRATED, FILLABLE MEDICINE CONTAINER AND METHOD OF FILLING AN INJECTION SYRINGE ASSEMBLY

CROSS-REFERENCE TO RELATED APPLICATION

This, application is a section 371 of International Application No. PCT/US11/33253, filed Apr. 20, 2011, which was published in the English language on Oct. 27, 2011 under International Publication No. WO 2011/133672 which claims the benefit of U.S. Provisional Patent Application No. 61/326,034, filed Apr. 20, 2010, the disclosures of which are incorporated herein by reference.

BACKGROUND OF THE INVENTION

The present invention relates to an automatic injection syringe assembly having an integrated and fillable medicine container, such as a medicine cartridge.

The utility of automatic injection syringes collectively referred to as "autoinjectors" is to facilitate the onboard storage of a fluid medicament within a mechanism that provides an easy-to-use and automatic administration of an injectable drug solution or suspension. Often, such autoinjectors are provided with the drug pre-loaded into a syringe element or canister that has been prepared under sterile conditions at a factory. In other applications, the user prepares the drug solution and autoinjector just prior to administration of the injection. The former option depends on the pharmaceutical manufacturer to undertake a time consuming and expensive process to gain regulatory approval for the drug/autoinjector combination before that product can be marketed. Examples of such devices are the EpiPen® manufactured by Meridian Medical Technologies, Inc., Humira® manufactured by Owen Mumford Ltd. exclusively for Abbott Laboratories, Inc. and the SureClick® system marketed by Scandinavian Health Limited.

In most circumstances, a user has no options for dose adjustment, given that the product is sold as a "standardized unit dose" i.e., the dose is established at the factory. Thus, the "pre-filled" option does not afford any flexibility to the user. Moreover, only a limited number of therapeutic applications pass the financial hurdles that would justify a pharmaceutical manufacturer's decision to undertake a combination product program for a pre-loaded autoinjector. Such products offer the advantages of ease-of-use, as there is minimal preparation involved. Most products of such sort are single-use disposable items, a valuable convenience and safety afforded to an injecting patient.

Accordingly, there is still a need for an autoinjector having an easy to use and fillable medicine container that allows a user to easily fill the medicine container and adjust the dosage of the autoinjector in a cost effective, safe and economical manner. The present embodiments of the invention meet this need.

BRIEF SUMMARY OF THE INVENTION

In accordance with a preferred embodiment, the present invention provides an automatic injection syringe assembly that includes a housing, a medicine container and a conduit member. The medicine container is housed within the housing and includes a piston having an aperture at a distal end thereof. The conduit member is releasably connected to the housing and includes open proximal and distal ends. The open distal end of the conduit member is releasably engaged with the piston and in fluid communication with the piston aperture. A channel or conduit within the conduit member is in fluid communication with the open proximal end and the open distal end of the conduit member.

In accordance with another preferred embodiment, the present invention provides an automatic injection syringe assembly that includes a housing, a medicine container, and a conduit assembly. The medicine container is housed within the housing and includes a piston. The conduit assembly includes a conduit member and a rod. The conduit member is releasably connected to the housing and the piston. The conduit member including open proximal and distal ends and a conduit in fluid communication with the open proximal end and the open distal end. The rod includes a piercing distal end and is positioned within the conduit. The rod is moveable between a first position adjacent the piston to a second position extending through the piston.

In accordance with yet another preferred embodiment, the present invention provides a medicine container assembly for an injection device that includes a housing, a medicine container and a cooperating ratcheting mechanism. The medicine container is housed within the housing and includes a hollow body having a closed distal end, and a piston within the hollow body. The cooperating ratcheting mechanism is on the housing and the medicine container and allows the medicine container to move in only one direction relative to the housing.

In accordance with another preferred embodiment, the present invention provides a conduit assembly for an injection device that includes a conduit member, a locking collar and a rod. The conduit member includes open proximal and distal ends, a conduit in fluid communication with the open proximal and distal ends, a mid-section, a distal section having a recess along a portion of the distal section. The locking collar includes a hollow body having the conduit member received therein, a detent extending from the locking collar, and a radially inwardly extending flange engaged to move within the recess. The rod is positioned within the conduit of the conduit member to reduce the volumetric size of the conduit.

In accordance with a further preferred embodiment, the present invention provides a piston assembly that includes an elastomeric body and a valve. The body includes a proximal end portion having a recess, a distal end portion, an aperture extending axially through the body and in fluid communication with the recess, and an endless sidewall extending between the proximal end portion and the distal end portion. The valve is positioned within the aperture and extends through the aperture.

In accordance with yet another preferred embodiment, the present invention provides a method of filling an injection syringe assembly that includes the step of providing an injection syringe subassembly. The injection syringe subassembly includes a medicine container having a piston with an aperture extending axially through the piston, and a conduit member releasably connected to the piston. The method further includes the steps of connecting a syringe having a medicament therein to the conduit member, and dispensing the medicament from the syringe, through the conduit member and the aperture of the piston, and into the medicine container.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 2A is a side elevational cross-sectional view of the power pack subassembly of the automatic injection syringe assembly of FIG. 1 in an assembled state;

FIG. 2B is a side elevational cross-sectional view of the cartridge housing subassembly of the automatic injection syringe assembly of FIG. 1 in an assembled state;

FIG. 3A is a perspective view of the assembly of the power pack subassembly with the cartridge housing subassembly of the automatic injection syringe assembly of FIG. 1;

FIG. 3B is a perspective view of the automatic injection syringe assembly of FIG. 1 in a fully assembled state;

FIG. 9A is an enlarged perspective view of a nose housing of the cartridge housing subassembly of FIG. 1;

FIG. 9B is an enlarged cross-sectional perspective view of the nose housing of FIG. 9A;

FIG. 10 is an enlarged perspective view of a conduit member of the cartridge housing subassembly of FIG. 1;

FIGS. 13A-13C are side elevational cross-sectional views of the cartridge housing subassembly of FIG. 2B attached to a syringe illustrating the progression and movement of the medicine container within the cartridge housing subassembly during a filling operation;

DETAILED DESCRIPTION OF THE INVENTION

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. The term "distal" means towards the injection end, needle point end or bottom end of the autoinjector. The term "proximal" means towards the cap end or top end of the autoinjector. Unless specifically set forth herein, the terms "a," "an" and "the" are not limited to one element but instead should be read as meaning "at least one." The terminology includes the words noted above, derivatives thereof and words of similar import.

Figure 1:
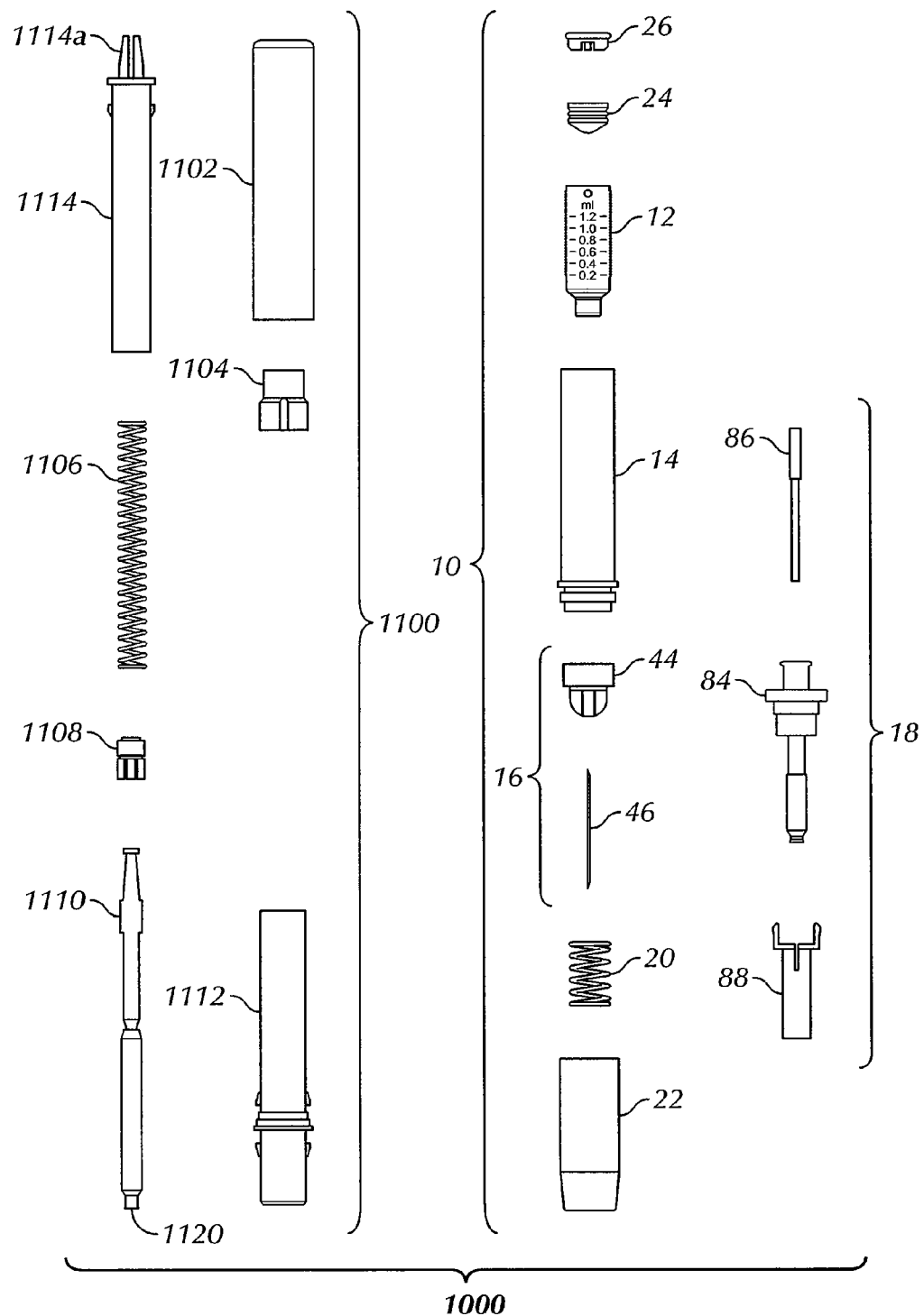
FIG. 1 is an exploded elevational view of a power pack subassembly and a cartridge housing subassembly of an automatic injection syringe assembly in accordance with a preferred embodiment of the present invention.

In a first preferred embodiment, the present invention provides an automatic injection syringe assembly 1000, as shown in FIGS. 1-3C. The automatic injection syringe assembly 1000 includes a power pack subassembly 1100 and a cartridge housing subassembly 10. FIG. 1 illustrates the various components of the power pack subassembly 1100 and the cartridge housing subassembly 10 in an exploded view. The overall housing 1001 (FIG. 3B) of the automatic injection syringe assembly 1000 is formed from the various housing components of the power pack subassembly and the cartridge housing subassembly. For example, the housing 1001 of the automatic injection syringe assembly can be formed from the cap, mid-housing, window tube and nose housing components, as further described below.

Figure 3C:
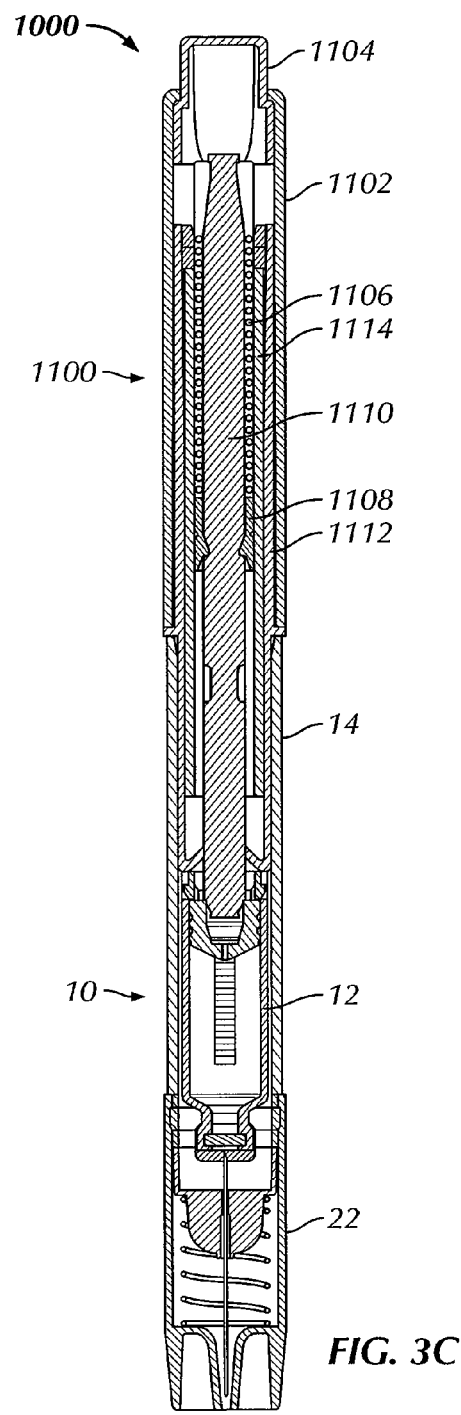
FIG. 3C is a side elevational cross-sectional view of the automatic injection syringe assembly of FIG. 3B.

Each of the power pack subassembly 1100 and the cartridge housing subassembly 10 are separate subassemblies that are assembled together after the cartridge housing subassembly 10 is filled with a medicament, as further described below. FIGS. 2A and 2B illustrate in a cross-sectional view the complete assembly of the respective subassemblies, while FIGS. 3A-3C illustrate the assembly of the two subassemblies. FIGS. 3B and 3C illustrate the fully assembled state of the power pack subassembly 1100 and the cartridge housing subassembly 10.

Referring to FIG. 3A, after the cartridge housing subassembly 10 is filled with a medicament (and removal of a conduit assembly 18, as described below is complete) the power pack subassembly 1100 is axially aligned with the cartridge housing subassembly 10 for assembly of the automatic injection syringe assembly 1000. Specifically, locking detents 1118 of the power pack subassembly 1100 are aligned with corresponding apertures 56a, 56b on the cartridge housing subassembly such that the two subassemblies can be snap-fitted together as shown in FIG. 3B.

Referring to FIGS. 1 and 3C, the power pack subassembly 1100 includes a cap 1102, a button 1104, a biasing member 1106, a spring rest 1108, a plunger rod 1110, a mid-housing 1112, and an inner housing 1114. The power pack subassembly 1100 is assembled together as shown in FIG. 2A. FIG. 3C illustrates the power pack subassembly 1100 in the assembled and ready-to-use state and assembled to the cartridge housing subassembly 10.

In the assembled state, the spring rest 1108 is releasably connected to the middle portion of the plunger rod 1110 by cooperating detents. The plunger rod 1110 and spring rest 1108 are positioned within the inner housing 1114 with the biasing member or injection spring 1106 in between the proximal end of the inner housing 1114 and an outer surface of the spring rest 1108. The injection spring 1106 is maintained in a compressed state by catches 1114a on the inner housing 1114 that retain the proximal head of the plunger rod 1110. The button or actuation button 1104 is positioned about the top of the proximal end of the inner housing 1114 and the cap 1102 and functions to release the catches 1114a to thereby release the injection spring 1106 upon depression. The foregoing assembly resides within the mid-housing 1112 and cap 1102

The power pack subassembly 1100 is similar in structure, operation and function to the power pack subassembly discussed in detail in U.S. Pat. No. 6,387,078 and U.S. Patent Application Publication Nos. 2011/0034879 and 2010/0185148, the entire disclosures of which are incorporated herein by reference in their entirety. However, the mid-housing 1112 differs slightly in that the mid-housing includes a flange 1116 extending radially outwardly from the mid-housing 1112 which serves as an abutment for the cap 1102. The mid-housing 1112 also includes locking detents 1118 positioned distal to the flange 1116, preferably in the form of outwardly extending bumps each having a sloped surface 1118a. The detents 1118 are configured to engage corresponding detents 56a, 56b (FIG. 7A) in the cartridge housing subassembly 10, preferably in the form of apertures in the window tube 14 that receive and lock the power pack subassembly 1100 thereto. The sloped surfaces 1118a of the detents 1118 facilitate the insertion of the distal portion of the mid-housing 1118 within the cartridge housing subassembly 10 such that the detents 1118 can engage the corresponding apertures 56a, 56b of a window tube 14. Additionally, the mid-housing 1112 includes locking detents 1117 positioned proximal to the flange 1116 to locking engage to the cap 1102. The locking detents 1117 are configured similarly to locking detents 1118, but with a sloped surface that slopes in the proximal and radially inwardly direction.

The plunger rod 1110 also includes a distal tip 1120 configured to have a substantially complementary shape to that of a proximal recess 24b on a piston 24 for engaging therewith, as further discussed below. Furthermore, the distal tip 1120 includes an outwardly extending rib 1122 (FIG. 2A) that can engage with the piston 24 and a substantially horizontal distally facing end. The substantially horizontal distally facing end facilitates the sealing of an aperture 24a extending through the piston 24, as further discussed below.

The cartridge housing subassembly 10 includes a medicament or medicine container 12, the window tube 14, a needle hub assembly 16, a conduit assembly 18, a return biasing member 20, and a nose housing 22, as shown in FIG. 1. The cartridge housing subassembly 10 is assembled together, as best shown in FIG. 2B.

Figure 4B:
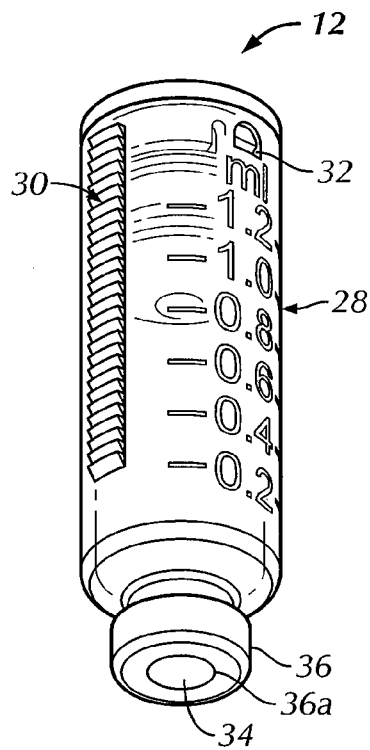
FIG. 4B is a top perspective view of the medicine container of FIG. 4A.
Figure 4A:
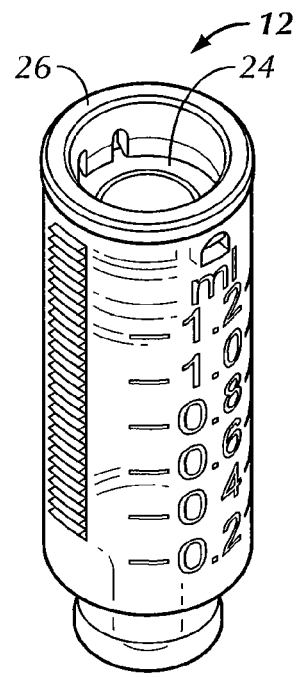
FIG. 4A is a bottom perspective view of a medicine container of the cartridge housing subassembly of FIG. 1.

The medicine container 12 is configured, as best shown in FIGS. 4A and 4B, and is positioned within the housing 1001 of the automatic injection syringe assembly 1000, e.g., the window tube 14. The medicine container 12 includes a hollow body, an open proximal end and a closed distal end. The medicine container 12 also includes a piston 24 configured to mount within and slide axially within the hollow body of the medicine container 12, and an end cap 26. The end cap 26 (FIG. 5) is a tubular end cap and mounts within the medicine container 12 about its proximal end to prevent the piston 24 from withdrawing completely out of the medicine container 12.

Graduations 28 are marked on the outside surface of the medicine container 12 to indicate volume fill. Moreover, the medicine container 12 is formed out of a clear or translucent material so as to have walls which enable a user to visually assess the quantity of medicament being filled within the medicine container 12. This is a key aspect of the present invention, because as the medicine container 12 is housed within the cartridge housing subassembly 10, the widow tube 14 allows for visual observation of the medicine container 12, thereby providing users the capability of visually monitoring the filling process of the medicine container 12. By way of example only, and not by way of limitation, the medicine container 12 can be made from a clear plastic, e.g., polypropylene, polyethylene terephthalate (PET), polyvinyl chloride, and combinations thereof.

The medicine container 12 further includes ratcheting features 30 configured as a plurality of sloped teeth that slope in the distal and radially inwardly direction i.e., tapers in the distal direction. The plurality of sloped teeth form part of a cooperating ratcheting mechanism for moving the medicine container 12 distally only within the cartridge housing subassembly 10, as further described below. The ratcheting features 30 are configured to extend in an axial direction along a longitudinal section of an exterior/outside surface of the medicine container 12 and preferably as a pair of ratcheting features that are positioned diametrically apart from each other about the external surface of the medicine container 12. The ratcheting features 30 engage the pawls of ratcheting members 58, as further described below.

The medicine container 12 also includes an aperture 32 about its proximal end, and preferably a pair of diametrically opposed apertures 32. The aperture 32 is configured to engage a corresponding detent of the end cap 26 to secure the end cap 26 thereto.

About the distal end of the medicine container 12 is a pierceable septum 34 retained within an open distal end of the medicine container 12 and secured therein by a cap 36, such as a crimpable cap that is well known in the art for medicine cartridges. The cap 36 is configured with a central through hole 36a to allow for the passage of a needle 46 therethrough and through the septum 34 in a manner well known in the art.

Figure 5:
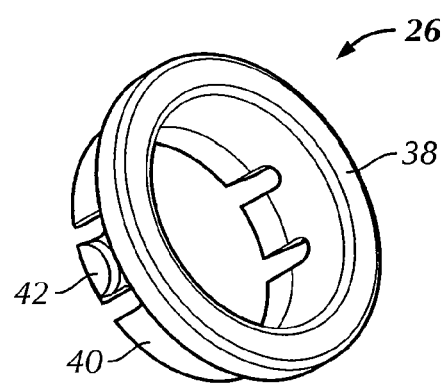
FIG. 5 is an enlarged perspective view of an end cap of the cartridge housing subassembly of FIG. 1.

The end cap 26 of the cartridge housing subassembly 10 is configured, as best shown in FIG. 5. The end cap 26 includes a tubular body 38 and a shallow distal body segment 40 having a slightly smaller diameter than the tubular body 38. The tubular body 38 is configured to seat on top of the proximal end of the medicine container 12, as shown in FIG. 4B, while the distal body segment 30 is configured to reside within the medicine container 12 interior so as to provide an abutment preventing the complete withdrawal of the piston 24 from the medicine container 12. Extending radially outwardly from the distal body segment 40 is a detent 42, and preferably a pair of diametrically opposed detents, for engaging the aperture(s) 32 of the medicine container 12 to lock the end cap 26 in place. Further, the detent 42 is configured to have a distal taper or slope to facilitate the insertion of the distal body segment 40 and the detents 42 into the aperture(s) 32.

Figure 4C:
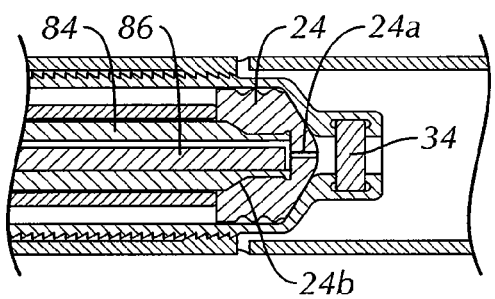
FIG. 4C is an enlarged partial side elevational cross-sectional view of the medicine container of FIG. 4A assembled within the cartridge housing subassembly of FIG. 2B.

In one embodiment, the piston 24 is configured, as best shown in FIGS. 2B and 4C, and housed within the medicine container 12 to slidably move therein, in a manner well known in the art. The piston 24 is an elastomeric piston and includes a body 25 having a recessed proximal end 24b configured to engage and receive a distal end of a conduit member 84 (see FIG. 1). That is, the proximal end portion of the piston 24 has a recess 24b (similar to recess 224b of piston 224—FIG. 15D) for receiving a distal end of the conduit member 84 or the plunger rod 1110. The body 25 also includes an endless sidewall extending between the proximal end portion and the distal end portion of the piston 24.

The proximal end of the piston 24 is also shaped to releasably connect to the distal end of the conduit member 84, such as by a slight undercut that engages a rib or flange about the distal end of the conduit member 84. The releasable engagement between the piston 24 and the open distal end of the conduit member 84 is sufficient to maintain a connection during a filling operation, as further described below, but slight enough such that the conduit member 84 can be withdrawn from the medicine container 12 without withdrawing the piston 24 from the medicine container 12. As discussed above, the end cap 26 also facilitates retention of the piston 24 within the medicine container 12 during removal of the conduit assembly 18 from the cartridge housing subassembly 10.

The piston 24 includes a distal end portion having an aperture 24a extending axially through the body 25 so as to be in fluid communication with the recess 24b of the proximal end of the piston 24 (FIG. 4C). As such, the piston 24 has an open proximal end and an open distal end i.e., an aperture 24a at its distal end. The aperture 24a is preferably positioned to be coaxial with the piston 24 and the recessed proximal end 24b, thereby allowing for fluid communication through the piston 24 and with the open distal end of the conduit member 84 and a conduit 93 for the conduit member 84 (see FIG. 2B) when assembled therewith. The aperture 24a is a key feature of the present embodiment in that it advantageously allows for fluid transfer from the conduit 93 of the conduit member 84 into the interior chamber of the medicine container 12. That is, the present embodiment allows a user to transfer a medicament to the interior chamber of the medicine container 12 from the outside thereof by way of a passageway through the piston 24.

In operation and during an injection, the aperture 24a is sealed off and prevented from allowing the passage of medicament back through the aperture 24a from the medicine container 12. This is accomplished by the distal end face of the plunger rod 1110 abutting the open proximal end of the piston 24 formed by the aperture 24a during an injection and the hydrostatic pressure of the medicament on the distal face of the piston 24 causing radial deformation of the piston 24 and subsequent closure of the aperture 24a. The radial deformation of the piston 24 results from hydrostatic pressure applied to the conical shaped tip of the piston 24 that points in the distal direction, which thereby results in radial forces directed to the piston 24 to radially deform its distal end and close/seal the aperture 24a.

Figure 6A:
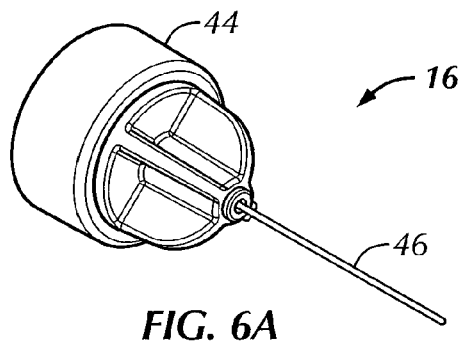
FIG. 6A is an enlarged bottom perspective view of a needle hub assembly of the cartridge housing subassembly of FIG. 1.
Figure 6B:
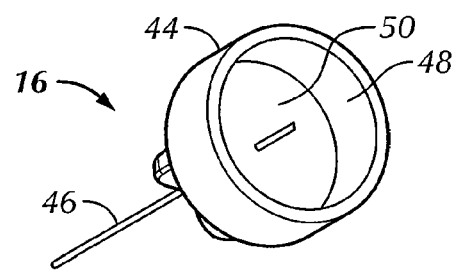
FIG. 6B is an enlarged top perspective view of the needle hub assembly of FIG. 6A.

The needle hub assembly 16 is configured, as best shown in FIGS. 6A and 6B, and includes a needle hub 44 and a needle 46. The needle 46 includes a distal piercing end and a proximal piercing end and mounts within the needle hub 44 in a manner well known in the art. Specifically, the needle 46 mounts within the needle hub 44 such that the needle 46 extends both distally from the needle hub 44 and in the proximal direction from the needle hub 44. The needle hub 44 is configured to have an open proximal end 48 with a generally tubular shape and a generally planar distal wall 50 substantially transverse to a longitudinal axis of the needle hub 44. As shown in FIG. 6B, the needle 46 extends proximally from the distal wall 50.

Figure 8:
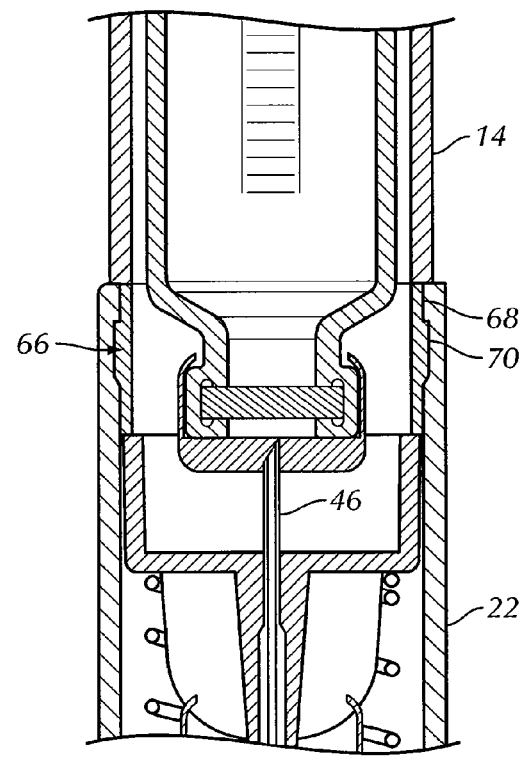
FIG. 8 is an enlarged partial side elevational cross-sectional view of the needle hub assembly adjacent to a filled medicine container of the cartridge housing subassembly.

The open proximal end of the needle hub 44 is sized and shaped to receive the distal end of the medicine container, as shown in FIG. 8. That is, during the injection phase, the distal end of the medicine container 12 abuts the distal wall 50 of the needle hub 44. At this position, the needle 46 being of sufficient length, extends completely through the septum 34 so as to be in fluid communication with the medicine container interior chamber.

As shown in FIG. 2B, the needle hub assembly 16 is mounted within the nose housing 22 having the return biasing member 20 disposed between the needle hub assembly 16 and the nose housing 22 and in a slightly compressed state. Preferably, the return biasing member 20 is a compression spring. The needle hub assembly 16 is prevented from moving proximally out of the nose housing 22 as a result of the distal end of the window tube 14 being received within the proximal end of the nose housing 22 thereby providing an abutment for the needle hub assembly 16.

Figure 7A:
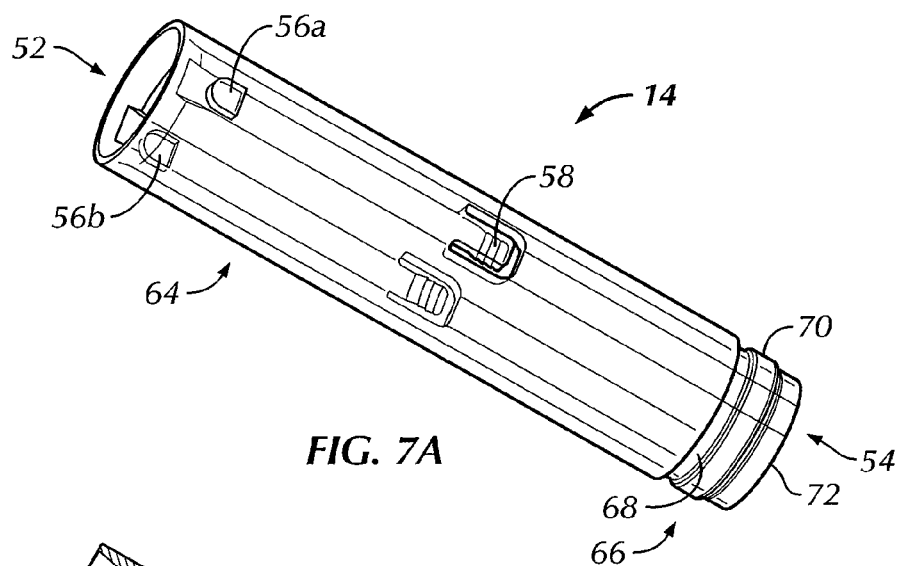
FIG. 7A is an enlarged perspective view of a window tube of the cartridge housing subassembly of FIG. 1.
Figure 7B:
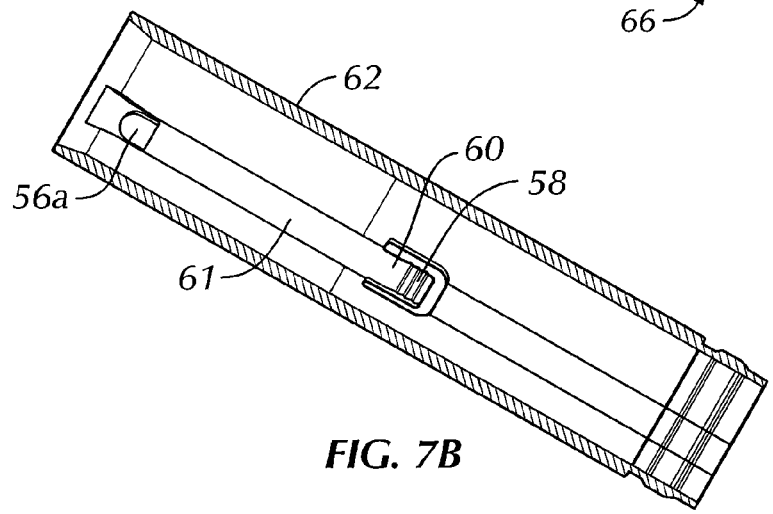
FIG. 7B is an enlarged cross-sectional perspective view of the window tube of FIG. 7A.

The window tube 14 is configured, as best shown in FIGS. 7A and 7B. The window tube 14 is a tubular member having an open proximal end 52 and an open distal end 54. The window tube 14 is also formed out of a clear or translucent material so as to have walls which enable a user to see through the window tube 14 in order to visually monitor the quantity of medicament being filled within the medicine container 12. By way of example only, and not by way of limitation, the window tube can be made from a clear plastic, e.g., polypropylene, polyethylene terephthalate (PET), polyvinyl chloride, and combinations thereof.

The window tube 14 also includes a pair of diametrically opposed apertures 56a and 56b about the open proximal end for receiving respective ends of locking collar detents 122, as further described below. Additionally, the window tube 14 includes a ratcheting member 58 formed on a tongue 60 cut out of and extending from the window tube sidewall 62. The ratcheting member 58 is formed along the interior surface of the tongue 60. Preferably, the window tube 14 includes a pair of ratcheting members 58 positioned about a mid-portion of the window tube 14 and diametrically opposed from each other. The ratcheting members 58 are also preferably positioned in axial alignment with the apertures 56a and 56b, respectively.

The ratcheting members 58 are configured as one or more pawls extending generally in the radially inwardly direction from the widow tube 14 to engage with the ratcheting features 30 of the medicine container 12. Collectively, the ratcheting members 58 and ratcheting features 30 are cooperating ratcheting mechanisms on the housing 1001 and the medicine container 12 of the automatic injection syringe assembly 1000 configured to allow the medicine container 12 to move only in one direction (i.e., the distal direction) relative to the housing 1001

The ratcheting features of the window tube 14 and medicine container 12 are rotationally aligned as a result of an axially extending groove 61 that is aligned with the tongue 60 and ratcheting member 58. The groove 61 is recessed within the sidewall 62 and sized to have a width sufficient to receive the ratcheting features 30 on the medicine container 12. Preferably, the groove 61 extends substantially the entire length of the widow tube 14.

The window tube 14 has a main body portion 64 and a distal body portion 66 (FIG. 7A). The distal body portion 66 includes a one or more recesses 68 and an annular rib or raised portion 70 formed on the outside surface thereof. Preferably, the recess 68 is an annular recess. The overall diameter of the distal body portion 66 is less than that of the overall diameter of the main body portion 64 and sized to allow for insertion of the distal body portion 66 into the open proximal end of the nose housing 22 (see FIG. 8). The configuration of the outside profile of the distal body portion 66 allows for a snap-fit assembly with the nose housing 22. The distal end of the window tube 14 i.e., the distally facing surface 72 serves as an abutment against which the needle hub 44 is biased against by the return biasing spring 20 (FIG. 2B).

The nose housing 22 is configured, as best shown in FIGS. 9A and 9B. The nose housing 22 forms the distal end of the automatic injection syringe assembly 1000. Generally, the nose housing 22 is configured to have a tubular shape, preferably with a slight taper about its distal end. The nose housing 22 includes an open proximal end 74 and a distal end 76.

The nose housing 22 also includes an inner recess 78 proximate the open proximal end 74 and preferably formed as an annular recess. The inner proximal end of the nose housing 22 is configured to have a profile, in part due to the recess 78, that corresponds to the outer profile of the distal body portion 66 of the window tube 14 (see FIG. 8). The corresponding profiles of the nose housing 22 and window tube 14 distal body portion 66 allow for the assembly and fixation of the two components.

The distal end 76 of the nose housing 22 includes a floor 80 having a centrally located and distally extending funnel 82. The floor 80 substantially traverses the longitudinal axis of the nose housing 22 and serves as an abutment for a distal end of the return biasing member 20 (see FIG. 2B). The funnel 82 is open at its proximal and distal ends to allow for the passage of the needle 46 therethrough and extends distally, preferably as far as the distal end of the overall nose hosing tubular body.

The conduit assembly 18 includes the conduit member 84, a rod 86 and a locking collar 88, as shown in FIGS. 1 and 10-12. The conduit assembly 18 assembles together as shown in FIG. 2B, with the rod 86 housed within the conduit member 84 and the conduit member 84 partially housed within the locking collar 88. The conduit assembly 18 is also releasably connected to and extends from the proximal end of the cartridge housing subassembly 10. Specifically, the conduit member 84 is releasably connected to the housing 1001 via the window tube 14. In operation, the conduit assembly 18 is used to fill the medicine container 12 and is then removed completely from the remainder of the cartridge housing subassembly 10 prior to the cartridge housing subassembly 10 being assembled to the power pack subassembly 1100, as shown in FIGS. 3B and 3C.

The conduit member 84 is configured, as best shown in FIG. 10. The conduit member 84 includes an open proximal end 90, an open distal end 92 and a conduit 93 in fluid communication with the open proximal end 90 and the open distal end 92. The conduit member 84 also includes a radially outwardly extending flange 94 for engaging the window tube 14 (i.e., a portion of the housing), a mid-section 96 having a first width or diameter, a distal section 98 having a second width or diameter that is smaller than the first width or diameter of the mid-section 96, a recess 100 along a portion (and preferably an upper portion) of the distal section 98, and a receiving member 102 extending in the proximal direction from the mid-section 96. The flange 94 extends further radially outwardly than the overall width of the mid-section 96 and has an overall width greater than the overall width of the window tube 14.

The mid-section 96 of the conduit member has diametrically opposed flats 104a, 104b (i.e., flat lateral surfaces) that extend in the axial direction and for at least a portion of the sidewall of the mid-section 96. The flats 104a, 104b are configured to engage the proximal end of the locking collar 88, as further described below, to prevent the locking collar 88 from rotating relative to the conduit member 84 in the assembled state. While the present embodiment is configured with two flats 104a, 104b, the conduit member 84 can alternatively be configured with one or more flats, such as three or four flats.

The distal section 98 of the conduit member 84 includes the recess 100. The recess 100 is formed about the proximal end of the distal section 98. Preferably, the distal section 98 is configured as a tubular member with the recess 100 being a portion of the distal section 98 having a smaller overall outside diameter than the remainder of the distal section 98. A flange 106 forms the transition between the recess 100 and the remainder of the distal section 98. As further discussed below, the recess 100 receives a segment of the locking collar 88 and preferably slidably receives a segment of the locking collar 88.

The distal section 98 of the conduit member also includes an outwardly extending annular rib 95 (FIG. 10) about its most distal end for releasably engaging an undercut or groove formed in the recess 24b of the piston 24. The distal end of the distal section 98 is also generally configured to be complementary in shape to the recess 24b of the piston 24. For example, the distal end of the conduit member 84 can be configured with a chamfer so as to have a frustroconical shape for nesting within a frustroconical segment of the recess 24b of the piston 24.

Figure 15A:
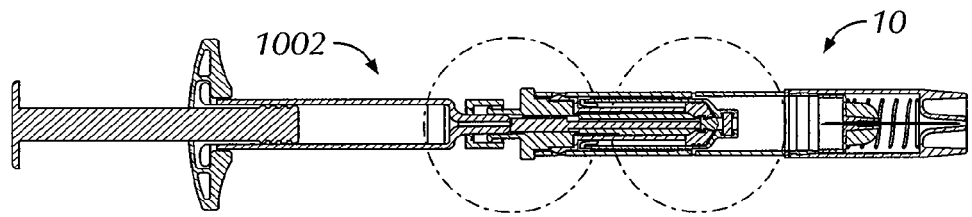
FIG. 15A is a side elevational cross-sectional view of the cartridge housing subassembly of FIG. 1 having an alternative piston design.
Figure 15B:
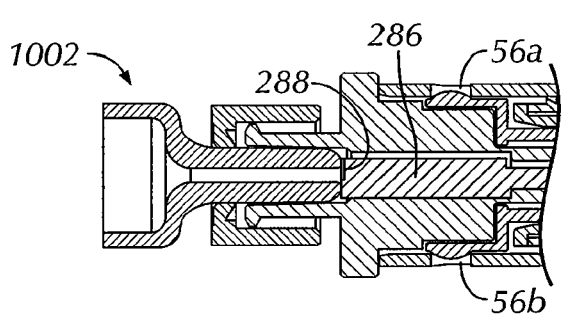
FIG. 15B is an enlarged partial side elevational cross-sectional view of a proximal end portion of the conduit assembly of FIG. 15A.

The receiving member 102 forms the proximal end of the conduit member 84. In general, the receiving member 102 is configured to releasably receive a distal end of a syringe, e.g., a needleless syringe. For example, the receiving member 102 can be configured as a female Luer-lok for receiving the male end of a Luer-lok syringe tip. FIG. 15A illustrates the connection of a syringe 1002 to the receiving member 102.

Figure 11B:
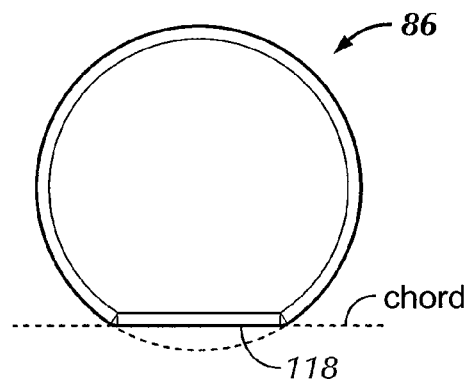
FIG. 11B is an enlarged top elevational view of the rod of FIG. 11A.
Figure 11A:
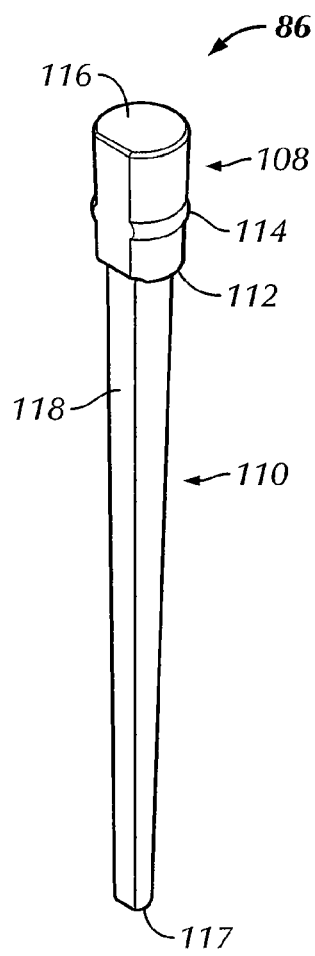
FIG. 11A is an enlarged top perspective view of a rod of the cartridge housing subassembly of FIG. 1.
Figure 15C:
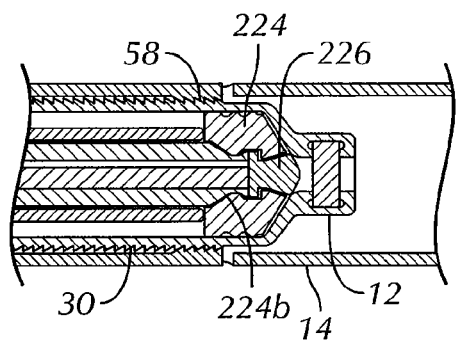
FIG. 15C is an enlarged partial side elevational cross-sectional view of a distal end portion of the conduit assembly of FIG. 15A.

The rod 86 is configured, as best shown in FIGS. 11A and 11B, and positioned within the conduit 93 of the conduit member 84 when in the assembled state (FIG. 2B). The rod 86 includes a proximal end segment 108 and a main body segment 110. The proximal end segment 108 is configured to have an overall width or diameter that is larger than the overall width of the main body segment 110, so as to form an overall slight inward taper of the rod 86 from the proximal end to the distal end. The rod 86 also includes a flange 112 that forms the transition from the proximal end segment 108 to the main body segment 110. The flange 112 serves as an abutment to secure removal of the rod 86 along with the conduit member 84, as further described below. The proximal end segment 108 also includes a substantially annular rib 114 about its mid-portion, a proximally facing surface 116 that forms the upper surface of the rod 86, and a distally facing end surface 117 that forms the lower surface of the rod 86. The distally facing end surface 117 can optionally include one or more grooves (similar to groove 288—FIG. 15C) to facilitate the flow of fluid from the conduit 93 to the aperture 24a during a filling operation.

The rod 86, while configured to have a generally cylindrical shape, includes a flat sidewall 118 that extends the entire axial length of the rod 86. The flat sidewall 118 is formed along the rod 86 such that the rod 86 has a shape defined by a major segment of a circle divided by a chord when viewed in cross-section, the cross-section being taken along a plane perpendicular to a major longitudal access of the rod 86, as shown in FIG. 11B.

Figure 12:
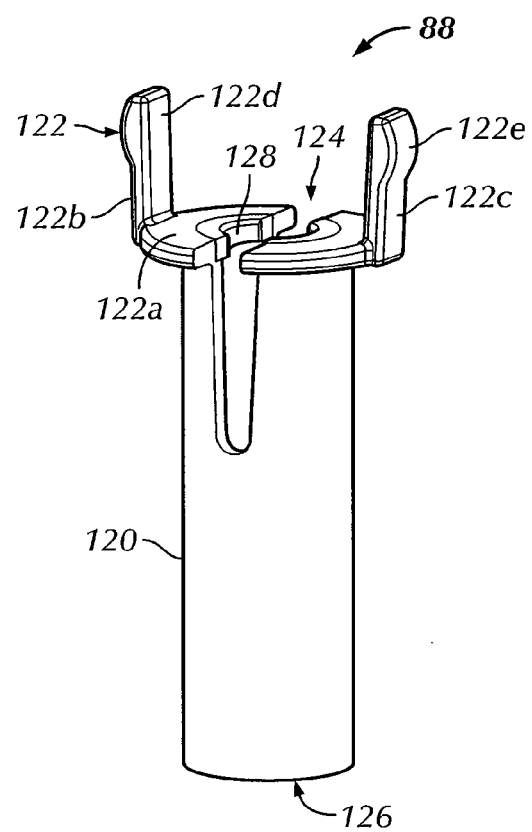
FIG. 12 is an enlarged perspective view of a locking collar of the cartridge housing subassembly of FIG. 1.

The locking collar 88 is configured, as best shown in FIG. 12, and includes a hollow body 120 and detents 122. The hollow body 120 includes an open proximal end 124 and an open distal end 126 and is generally configured as a tubular member. About the proximal end 124 is a radially inwardly extending flange 128. Extending in the proximal direction from the proximal end 124 of the hollow body 120 is a pair of detents 122. Specifically, the detents 122 extend radially outwardly from the hollow body 120 and then proximally from the hollow body 120. That is, each of the detents 122 includes a substantially planar base 122a and an elongated extension 122b that extends from the planar base 122a substantially perpendicular therefrom. Each of the elongated extensions 122b includes an outer surface 122c and an inner surface 122d. The inner surface 122d is a substantially flat surface configured to directly engage the respective flats 104a, 104b of the conduit member 84, such that in the assembled state, the conduit member 84 does not rotate relative to the locking collar 88.

About the outer surface of the elongated extensions 122b is a radially outwardly extending protrusion 122e for engaging the aperture 58a of the window tube 14 to thereby releasably lock the locking collar 88 in a fixed position such that the locking collar 88 does not translate rotationally or axially within the window tube 14 during its ready-to-use state or medicine container filling phase. Each protrusion 122e is preferably in the form of a bump or convex surface, as shown in FIG. 12. The detents 122 are preferably a pair of diametrically opposed detents that extend in the proximal direction a length no more than the axial length of the flats 104a, 104b of the conduit member and preferably to about a mid-region of the flats 104a, 104b. Owing to the elongated nature of the detents 122, the detents can flex radially inwardly to disengage from the window tube 14.

FIG. 2B illustrates a cross-section of the conduit assembly 18 in the fully assembled position within the cartridge housing subassembly 10 prior to use. Specifically, the conduit member 84 is configured to have its distal section 98 housed within the hollow body 120 of the locking collar 88 such that the radially inwardly extending flange 128 resides within the recess 100 for moving or sliding in the axial direction therein. In other words, the locking collar 88 has the conduit member 84 positioned therein. Furthermore, the locking collar 88 is rotationally aligned with the conduit member 84 such that the flats or inner surface 122d of the locking collar detents 122 engage the flats 104a, 104b of the conduit member 84 to prevent rotation relative to each other. That is, the mid-section 96 of the conduit member 84 is received between the pair of detents 122 of the locking collar 88 and the pair of detents 122 of the locking collar 88 engages the diametrically opposed flat lateral surfaces 104a, 104b of the mid-section 96.

The rod 86 resides within the conduit 93 of the conduit member 84 to reduce the volumetric size of the conduit 93. As shown in FIG. 2B, due to the flat surface 118 along the side of the rod 86, a predetermined passageway through the conduit 93 of the conduit member 84 is formed when the rod 86 is assembled therein. The predetermined passageway is in fluid communication between the open proximal end 90 and the open distal end 92 of the conduit member 84.

Furthermore, when in the fully assembled and prior to use configuration, as shown in FIG. 2B, the radially outwardly extending protrusions 122e of the locking collar 88 received within the apertures 56a, 56b of the window tube 14 prevent rotation of the locking collar 88 relative to the window tube 14. Moreover, the detents 122 are prevented from withdrawing from the apertures 56a, 56b by the presence of the mid-section 96 of the conduit member. That is, the overall width from flat to flat of the mid-section 96 is configured to be slightly smaller than the overall inside width between the inner surfaces 122d of the locking collar 88. This sizing of the corresponding conduit member 84 and the locking collar detents 122 prevent the detents 122 from withdrawing or being forced from the apertures 56a, 56b prematurely, or before withdrawal of the conduit member 84. Additionally, the radially inwardly extending flange 128 is received within the recess 100 of the conduit member 84, which serves to engage the flange 106 of the conduit member 84 during removal of the conduit assembly 18, as further discussed below.

The apertures 56a, 56b and detents 122 represent cooperating detents on the widow tube 14 (i.e., a portion of the housing 1001) and the locking collar 88, respectively that releasably hold the locking collar 88 in a fixed position with respect to the housing 1001. The fixed position of the locking collar in the housing 1001 represents a first position of the locking collar within the housing 1001. When in the first position, the detents 122 of the locking collar 88 are located proximate or adjacent the mid-section of the conduit member 84.

FIGS. 13A-13C illustrate the filling operation of the medicine container 12. As shown in the figures, a needless syringe 1002 is connected to the receiving member 102 of the conduit member 84. The needless syringe 1002 can be a Luer-lok syringe having a male syringe tip that sealingly engages the receiving member 102. Thereafter, a user injects medicament from the syringe 1002 into the conduit 93 of the conduit member 84, which thereafter passes through the conduit 93 and through the aperture 24a of the piston 24 and into the medicine container 12. As the medicine container 12 fills with medicament from the syringe, the medicine container 12 moves in the distal direction relative to the window tube 14 owing to pressure of fluid build up in the medicine container 12 and the cooperating ratcheting mechanisms of the medicine container 12 and the window tube 14. Thus, as shown in FIG. 13C, when the medicine container 12 is filled, the distal end of the medicine container 12 moves closer to or adjacent to the proximal end of the needle 46 extending from the needle hub 44. Moreover, as seen in the progression of FIGS. 13A-13C, as the medicine container 12 is filled and moves distally, the position of the piston 24 remains fixed due to engagement of the piston 24 with the distal end of the conduit member 84.

Figure 14A:
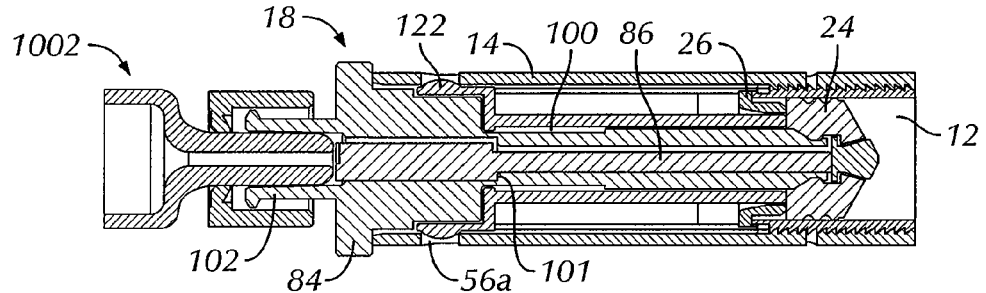
FIGS. 14A-14D are side elevational cross-sectional views of the cartridge housing subassembly of FIG. 2B attached to a syringe illustrating the removal of the conduit assembly from the remainder of the cartridge housing subassembly after a filling operation of the medicine container is completed.
Figure 14B:
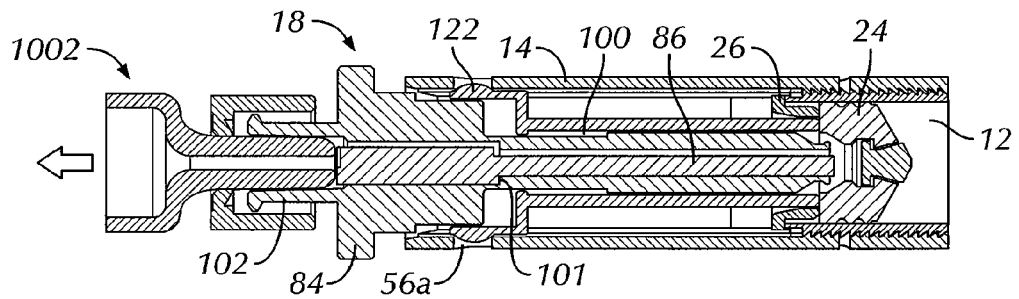

FIGS. 14A-14D illustrate the progression of the removal of the conduit assembly 18 from the reminder of the cartridge housing subassembly 10 after filling of the medicine container 12. FIG. 14A illustrates the distal end of the syringe 1002 connected to the receiving member 102 of the conduit member 84 immediately after filling of the medicine container 12 is complete. Afterwards, the syringe 1002, while still connected to the conduit member 84, is initially withdrawn or pulled away from the cartridge housing subassembly 10 (FIG. 14B). As the syringe 1002 is withdrawn or pulled in the proximal direction, the conduit member 84 moves proximally in tandem with the syringe 1002. At this time, the distal end of the conduit member 84 also disengages from the piston 24.

Figure 14C:
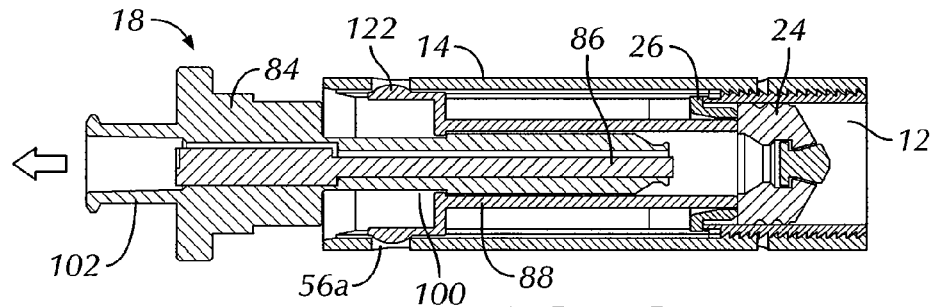
Figure 14D:
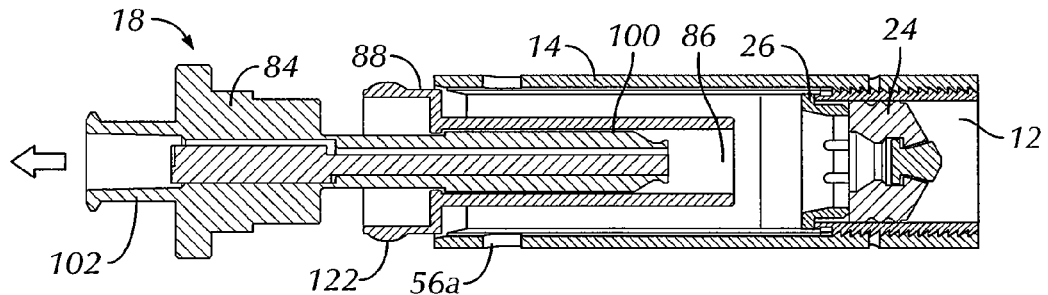

In this initial stage of withdrawal, the conduit member 84 moves first relative to the locking collar 88 (FIGS. 14B and 14C). That is, as the conduit member 84 is initially withdrawn, it moves from a first position wherein the detents 122 of the locking collar 88 are adjacent the mid-section 96 of the conduit member 84 to a second position relative to the locking collar 88. Specifically, the conduit member 84 moves from a first position where the radially inwardly extending flange 128 of the locking collar 88 is at a proximal position along the recess 100 to a second position wherein the flange 128 is at a distal position along the recess 100. Moreover, in the first position, the locking collar 88 abuts the piston 24, specifically a distal end of the locking collar 88 abuts a proximally facing end of the piston 24. Thus, as the conduit member 84 is initially withdrawn from the piston 24, thereby moving out of the first position and to the second position, the locking collar 88 impedes and prevents the upward (i.e., proximal direction) movement of the piston 24 out of the medicine container 12. The upward movement of the piston 24 being caused by the withdrawal of the conduit member 84 out of the cartridge housing subassembly 10 and the releasable engagement between the conduit member 84 and the piston 24.

Further, in the second position, the detents 122 of the locking collar 88 are displaced from the mid-section 96 of the conduit member 84 and the radially inwardly extending flange 128 of the locking collar 88 engages the distal end of the recess 100, such that the detents 122 are displaceable from the housing 1001 to allow the conduit member 84 to move from the second position to a third position out of the housing 1001. When moving from the second position to the third position, the conduit member 84 disengages the cooperating detents, as further described below.

In other words, as the conduit member 84 is initially withdrawn, it causes the flange 128 to slide or move axially along the recess 100. The distance that the radially inwardly extending flange 128 travels within the recess 100 is sufficient to allow the mid-section 96 of the conduit member 84 to move past the ends of the proximally extending detents 122 of the locking collar 88. Thus, as best shown in FIG. 14C, as the mid-section 96 moves past the detents of the locking collar 88, the detents 122 are then free to flex radially inwardly so as to be pulled out of or deflected out of the apertures 56a, 56b of the window tube 14, and are thereafter pulled out of the cartridge housing subassembly 10. A force is applied to the locking collar 88 as a result of the radially inwardly extending flange 128 engaging with the flange 106 or bottom portion of the recess 100 on the conduit member 84 (FIG. 14C). Thereafter, with continued withdrawal of the syringe 1002 away from the cartridge housing subassembly 10, the conduit assembly 18 is completely withdrawn from the cartridge housing subassembly 10 (see FIG. 14D). The rod 86 is retained within the conduit member 84 as a result of an inwardly extending ridge 101 (see FIG. 14A) of the conduit member 84 engaging with the flange 112 of the rod 86.

After the complete removal of the conduit assembly 18 from the remainder of the cartridge housing subassembly 10, the cartridge housing subassembly 10 is assembled to the power pack subassembly 1100, as described above. Upon assembly of the two subassemblies, a user is then ready to make an injection. This is accomplished by placing the distal end of the automatic injection syringe assembly 1000 against an injection site and simply pressing the actuating button 1104. Upon depressing the actuating button 1104, it causes the catches 1114a to separate thereby allowing the plunger rod 1110 to move distally due to the force of the injection spring 1106 acting on the spring rest 1108 that is connected to the plunger rod 1110. At the point where the injection phase is complete, the spring rest 1108 engages an internal surface of the mid-housing 1112 that causes the spring rest 1108 to disengage from the plunger rod 1110, thereby freeing the plunger rod 1100 from the force of the injection spring 1106. Further details regarding the operation of the automatic injection syringe assembly 1000 are disclosed in detail in U.S. Pat. No. 6,387,078 and U.S. Patent Application Publication Nos. 2011/0034879 and 2010/0185148, the entire disclosures of which are incorporated herein by reference in their entirety.

FIGS. 15A-15E illustrate an alternative embodiment of the conduit assembly and medicine container 12. In this embodiment, all features of the conduit assembly 84 and medicine container 12 are the same as that described in the above embodiment, except for the piston 224 and the rod 286. The piston 224 includes an aperture 224a extending axially through the piston 224 and positioned coaxial with the piston 224 and a recess 224a at its proximal end. Preferably, the aperture 224a is a conical shaped aperture that tapers radially inwardly in the proximal direction. The proximal recess 224b of the piston 224 is configured to receive and releasably engage the distal end of the conduit member 84 or a distal end of a plunger rod 86, such as plunger rod 1110.

The piston also includes a mechanical valve 226 positioned within the aperture 224a. The valve 226 is configured to move between an open position and a closed position. In the open position, the valve 226 allows for fluid communication through the piston 224, while in the closed position, the valve 226 seals off the aperture 224a preventing fluid transfer through the aperture 224a. The valve 226 is moved by being biased in either the distal direction, by the force of a rod pressing against the proximal end of the valve 226, or in the proximal direction by hydrostatic pressure of the fluid within the medicine container 12 during an injection phase.

Figure 15D:
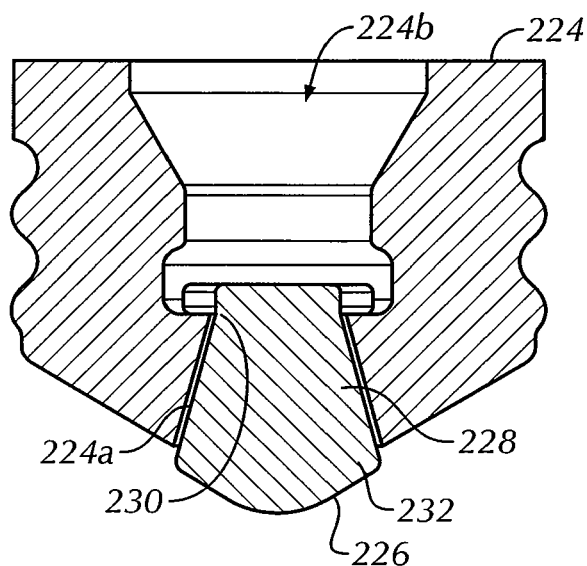
FIG. 15D is an enlarged side elevational cross-sectional view of a piston and a valve of the medicine container of FIG. 15A.
Figure 15E:
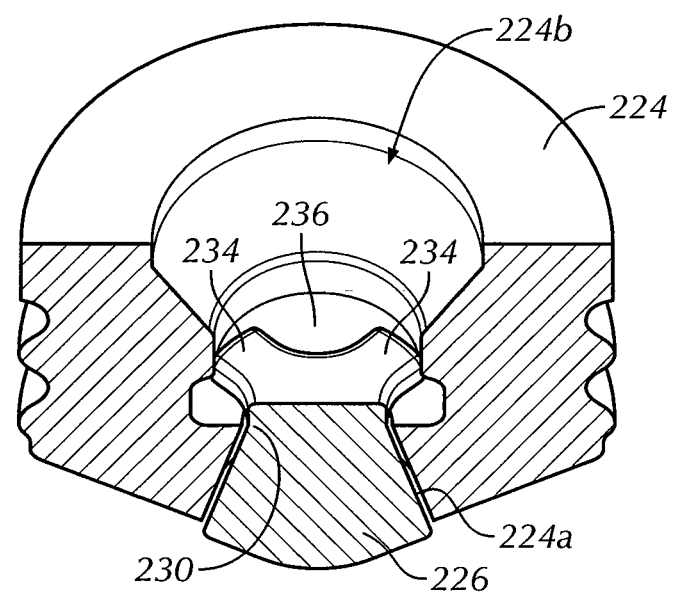
FIG. 15E is an enlarged perspective cross-sectional view of the piston and valve of FIG. 15D.

The valve 226 is preferably configured, as shown in FIGS. 15D and 15E. The valve includes a conical body 228 having a proximal end 230 and a distal end 232 and extends completely through the aperture 224a. The conical body 228 tapers radially inwardly in the proximal direction. The distal end 232 is configured with a convex outer surface. Extending from the proximal end of the conical body 228 are one or more radially outwardly extending finger-like members or branches 234. When more than one finger-like members 234 extends from conical body, a space or gap 236 is provided between them. The gap 236 extends to the proximal end 230 to allow for fluid communication between the aperture 224a and the recess 224b when the valve 226 is biased in the distal direction. The finger-like members are also formed to have a thickness sufficient to allow for easy fluid communication leading to the aperture 224a when the valve 226 is in the open position.

FIG. 15D and 15E, also illustrate the valve 226 as if a biasing force was applied to the valve 226 by the rod 286 biasing the valve in the distal direction or in a non-biased state, as further described below. This represents the open position of the valve 226. That is, the conical body 228 and the aperture 224a are sized and shaped to be complementary such that with a slight distally directed bias or even no bias, the valve 226 within the aperture 224a maintains an open fluid pathway through the piston 224. However, due to the complementary conical shape of the aperture 224a and the valve 226, during an injection, hydrostatic pressure of the fluid within the medicine container 12 exerts a proximally directed biasing force on the valve 226 biasing it in the proximal direction. When this occurs, the valve 226 sealingly engages the aperture 224a due to its complementary conical shape.

The rod 286 is similar to the rod 86, however, in this embodiment, the rod 286 is configured to be slightly longer. That is, the overall length of the rod 286 is such that when the syringe tip is fully engaged and inserted within the receiving member 102, the distal end of the syringe 1002 abuts and pushes the rod 286 distally. The distal end of the rod 286 then pushes down on the valve 226 to move the valve 226 to the open position or maintain the valve 226 in the open position. The rod 286 can optionally include a relief or a groove 288 extending radially outwardly about the proximal end face of the rod 286 to facilitate fluid communication between its proximally facing end and the conduit when the syringe 1002 is fully seated against the rod 286.

Figure 16A:
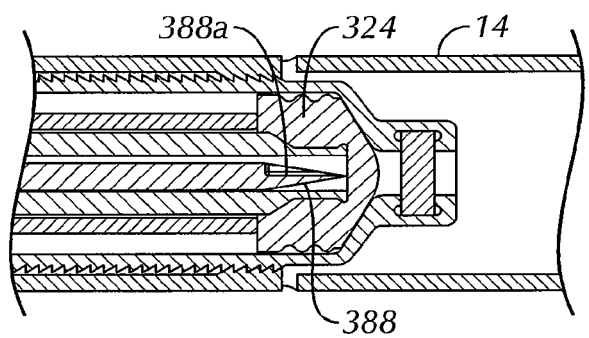
FIGS. 16A-16B are partial side elevational cross-sectional views of an alternative piston and conduit assembly embodiment of the cartridge housing subassembly of FIG. 1.
Figure 16B:
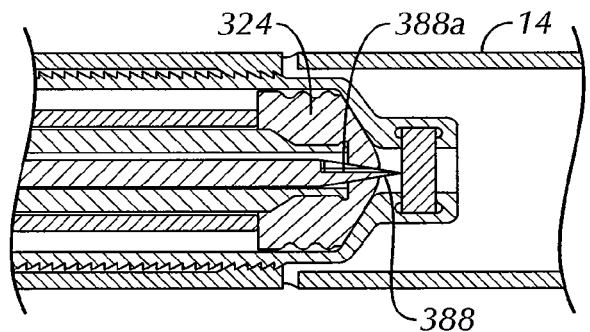

FIGS. 16A and 16B illustrate another embodiment of the conduit assembly and medicine container. In this embodiment, all features of the conduit assembly and medicine container are the same as that described in the above embodiments except for the piston 324 and the rod 386. The piston 324 is configured similar to the piston 24 except for the inclusion of an aperture extending through the piston, such as aperture 24a for piston 24. That is, the piston 324 does not include any axially extending aperture.

The rod 386 includes a sharp distal tip 388 i.e., a piercing distal end, for piercing through the piston 324. The distal tip of the rod 386 is configured to have a beveled or angled tip along with an axially extending recess or groove 388a to allow fluid communication therethrough and through the piston 324 when extended through the piston 324. Specifically, as shown in FIG. 16B, the length of the groove 388a extending in the axial direction is greater than the axial thickness of the piston 324 through which the rod 386 is intended to pierce through.

The rod 386 is similar to the rod 286, however, in this embodiment, the rod 386 is configured to have an overall length such that when the syringe tip is fully engaged and inserted within the receiving member 102, the distal end of the syringe 1002 abuts and pushes the rod 386 distally. The distal end of the rod 386 then pierces completely through the piston 324 creating a passageway for fluid communication through the piston 324. In other words, the rod 386 is moveable between a first position within the conduit that is spaced from or adjacent the piston 324 to a second position extending completely through the piston 324.

In another aspect, the present invention provides a medicine container assembly for an injection device that includes a housing, a medicine container and cooperating ratcheting mechanisms. The housing can be as described above for the housing of the automatic injection syringe assembly 1000. The medicine container is retained within the housing and can be as described above for medicine container 12. Thus, the medicine container 12 includes a hollow body having a closed distal end and a piston within the hollow body of the medicine container. The medicine container assembly also includes cooperating ratcheting mechanisms on the housing and the medicine container to allow the medicine container to move in only one direction. The cooperating ratcheting mechanisms can be as described above for the automatic injection syringe assembly 1000.

In yet another aspect, the present invention provides a piston assembly, such as a piston assembly for a medicine container e.g., a medicine cartridge. The piston assembly includes an elastomeric body and a valve. The body can be as describe above for the automatic injection syringe assembly 1000. Thus, the body includes a proximal end portion having a recess for receiving a plunger rod and a distal end portion having an aperture extending axially through the body and which is in fluid communication with the recess. Furthermore, the body includes an endless sidewall extending between the proximal end portion and the distal end portion. The valve can be as described above for valve 226.

In a further aspect, the present invention provides a method of filling an injection syringe assembly that includes the step of providing an injection syringe subassembly having a medicine container and a conduit member. The medicine container and conduit member can be as described in the above embodiment for the automatic injection syringe assembly 1000. Thus, the medicine container includes a piston with an aperture extending axially through the piston. The conduit member is releasably connected to the piston. The method also includes the step of dispensing the medicament from the syringe, through the conduit member and the aperture of the piston, and into the medicine container.

The injection syringe subassembly can optionally be an injection syringe subassembly that is integral with an autoinjector assembly. That is, the injection syringe subassembly be formed as part of a complete autoinjector assembly (i.e., a completely assembled autoinjector assembly), such as the automatic injection syringe assembly 1000.

Additionally, the method includes the steps of withdrawing the conduit member from the medicine container after the dispensing step and providing an injection mechanism subassembly. The injection mechanism subassembly can be as described above for the power pack subassembly 1100. Thus, the injection mechanism subassembly includes a driving member and a plunger rod connect to and driven by the driving member. Furthermore, the method includes the step of assembling the injection mechanism subassembly to the injection syringe subassembly, thereby connecting the plunger rod to the piston.

It will be appreciated by those skilled in the art that changes could be made to the embodiments described above without departing from the broad inventive concept thereof. It is to be understood, therefore, that the present invention is not limited to the particular embodiments disclosed, but it is intended to cover modifications within the spirit and scope of the present invention as set forth in the appended claims.

We claim:

1. An automatic injection syringe assembly comprising:
   a housing;
   a medicine container movable within the housing, the medicine container includes a piston therein having an aperture at a distal end thereof; and
   a conduit member releasably connected to the housing and the piston, including open proximal and distal ends, said open distal end being releasably engaged with the piston and in fluid communication with the aperture and a conduit in fluid communication with the open proximal end and the open distal end;
   a locking collar having the conduit member positioned therein; and
   cooperating detents on the housing and the locking collar to releasably hold the locking collar in a fixed position with respect to the housing.

2. An automatic injection syringe assembly comprising:
   a housing;
   a medicine container movable within the housing, the medicine container includes a piston therein having an aperture at a distal end thereof; and
   a conduit member releasably connected to the housing and the piston, including open proximal and distal ends said o en distal end being releasably engaged with the piston and in fluid communication with the aperture, and a conduit in fluid communication with the open proximal end and the open distal end, wherein the conduit member further comprises:
   a radially outwardly extending flange for engaging the housing;
   a mid-section having a first width;

a distal section having a second width smaller than the first width; and a recess along a portion of the distal section.

3. The automatic injection syringe assembly of claim 2, wherein the conduit member further comprises a receiving member extending proximally from the mid-section and configured to releasably receive a distal end of a syringe.

4. The automatic injection syringe assembly of claim 2, further comprising:

a locking collar that includes a hollow body having the conduit member positioned therein; and cooperating detents on the housing and the locking collar to hold the locking collar in a first position within the housing.

5. The automatic injection syringe assembly of claim 4, wherein in the first position, the cooperating detents of the locking collar are located proximate the mid-section of the conduit member.

6. The automatic injection syringe assembly of claim 4, wherein the locking collar includes a radially inwardly extending flange received within the recess of the conduit member, and wherein the cooperating detents of the locking collar extend radially outwardly from the hollow body.

7. The automatic injection syringe assembly of claim 6, wherein the conduit member is movable from a first position wherein the cooperating detents are adjacent the mid-section of the conduit member to a second position relative to the locking collar, and wherein in the second position, the cooperating detents of the locking collar are displaced from the mid-section of the conduit member and the radially inwardly extending flange of the locking collar engages a distal end of the recess, such that the cooperating detents are displaceable from the housing to allow the conduit member to move from the second position to a third position out of the housing.

8. The automatic injection syringe assembly of claim 7, wherein the locking collar abuts the piston to impede movement of the piston as the conduit member moves from the first position to the second position.

9. The automatic injection syringe assembly of claim 7, wherein when moving from the second position to the third position, the conduit member disengages the cooperating detents.

10. An automatic injection syringe assembly comprising:

a housing;

a medicine container moveable within the housing, the medicine container includes a piston; and a conduit assembly that includes:

a conduit member releasably connected to the housing and the piston, including open proximal and distal ends, said open distal end being releasably engaged with the piston and in fluid communication with an aperture, and a conduit in fluid communication with the open proximal end and the open distal end, and a rod that includes a piercing distal end, wherein the rod is positioned within the conduit and moveable between a first position adjacent the piston and a second position extending through the piston;

a locking collar having the conduit member positioned therein; and cooperating detents on the housing and the locking collar to releasably hold the locking collar in a fixed position with respect to the housing.

\* \* \* \* \*